United States Patent [19]

Martin et al.

[11] 4,019,727
[45] Apr. 26, 1977

[54] HEAD SUPPORT AND RESTRAINING APPARATUS

[75] Inventors: William O. Martin, Chesterland; Harry Derda, Beachwood, both of Ohio

[73] Assignee: Case Western Reserve University, Cleveland, Ohio

[22] Filed: Nov. 20, 1975

[21] Appl. No.: 633,840

[52] U.S. Cl. .............................................. 269/328
[51] Int. Cl.$^2$ ...................................... A61G 13/00
[58] Field of Search ............... 269/328, 71, 94, 74, 269/157, 246

[56] References Cited

UNITED STATES PATENTS

| | | | |
|---|---|---|---|
| 2,535,559 | 12/1950 | Wolf | 269/328 |
| 3,099,441 | 7/1963 | Ries | 269/328 |
| 3,319,954 | 5/1967 | Shevick et al. | 269/328 |
| 3,521,057 | 7/1970 | Morlin | 269/328 |
| 3,650,523 | 3/1972 | Darby | 269/328 |
| 3,806,110 | 4/1974 | Glasser et al. | 269/328 |

*Primary Examiner*—Al Lawrence Smith
*Assistant Examiner*—Robert C. Watson
*Attorney, Agent, or Firm*—Gardner and Anten

[57] ABSTRACT

An apparatus for supporting and restraining the head of a patient (typically an infant) during medical treatment, for example, during the delivery of continuous positive airway pressure to a patient suffering from a respiratory disease. The apparatus of the preferred embodiment of the present invention includes a generally arcuate cradle, a pair of opposed, generally flexible restraining plates pivotably mounted within the cradle for conforming to and positively restraining the patient's head, and adjustable means on the cradle for moving the restraining plates toward one another to a position wherein they will gently, yet firmly, restrain the patient's head. Padding of a suitable material (e.g., lamb's wool) lines the interior exposed surfaces of the members and the cradle to cushion the patient's head. The padding may be held within the apparatus by means of cooperating mating strips of velcro. The generally arcute cradle is mounted in a generally arcuate groove in the upper surface of a base member by means of a suitable clamp which may be loosened to permit the cradle to be rotated until the patient's head is in a desired angular position and which, when tightened, will lock the cradle in the desired angular position.

12 Claims, 3 Drawing Figures

HEAD SUPPORT AND RESTRAINING APPARATUS

FIELD OF THE INVENTION

The present invention relates to an apparatus for holding and restraining a patient's head during medical treatment.

BACKGROUND OF THE INVENTION

In the medical field there exists a need for an improved device for gently and yet firmly holding and restraining a patient's head in one of a number of fixed angular positions during medical treatment.

One example of medical treatment wherein such a head holding and restraining device is required is in the delivery of continuous positive airway pressure to a patient (often an infant) suffering from a respiratory disease. Continuous positive airway pressure is typically delivered to the patient through a nasal cannula which must be inserted and held within the patient's nose. A head holding and restraining apparatus is required to prevent the infant or other patient from turning his head and partially or fully removing the nasal cannula from his nose.

One requirement of such a head holding and restraining device is that it be adapted to permit a doctor or nurse to move the patient's head, from time-to-time, to one of a number of angular positions.

While there have been attempts to design head holding and restraining apparatus prior to the advent of the present invention, none has proven to be entirely satisfactory or efficient in use.

Accordingly, it is an object of the present invention to provide a head holding and restraining apparatus for gently and yet firmly holding a patient's head in any one of a number of fixed angular positions during medical treatment.

SUMMARY OF THE PREFERRED EMBODIMENT

The foregoing and other objects of the present invention have been realized by providing a generally arcuate or U-shaped cradle member mounted for arcuate or angular movement on a base member. An adjustabe clamp is provided for locking and the cradle member in a desired angular position. The clamp, when loosened, permits the generally arcuate cradle to be rotated to any desired position. When the desired angular position of the cradle has been reached, the clamp is tightened to lock the cradle in such angular position.

A pair of opposed, generally flexible, generally arcuate head restraining plates are mouted within the generally arcuate cradle member on either side thereof by means which permit the upper portions of the generally flexible restraining plates to pivot inwardly, toward one another, to accommodate, conform to and restrain the patient's head in place. Adjustment means are provided for selectively moving the generally flexible head restraining plates toward one another to hold the patient's head.

A suitable padding, such as lamb's wool, for example, lines the interior exposed surfaces of the restraining plates and the cradle to cushion the patient's head.

Other objects and numerous advantages of the head supporting and restraining apparatus of the present invention will be realized from a review of the following detailed description of a preferred embodiment of the apparatus of the present invention.

DETAILED DESCRTIPTION OF A PREFERRED EMBODIMENT

Figure 1:
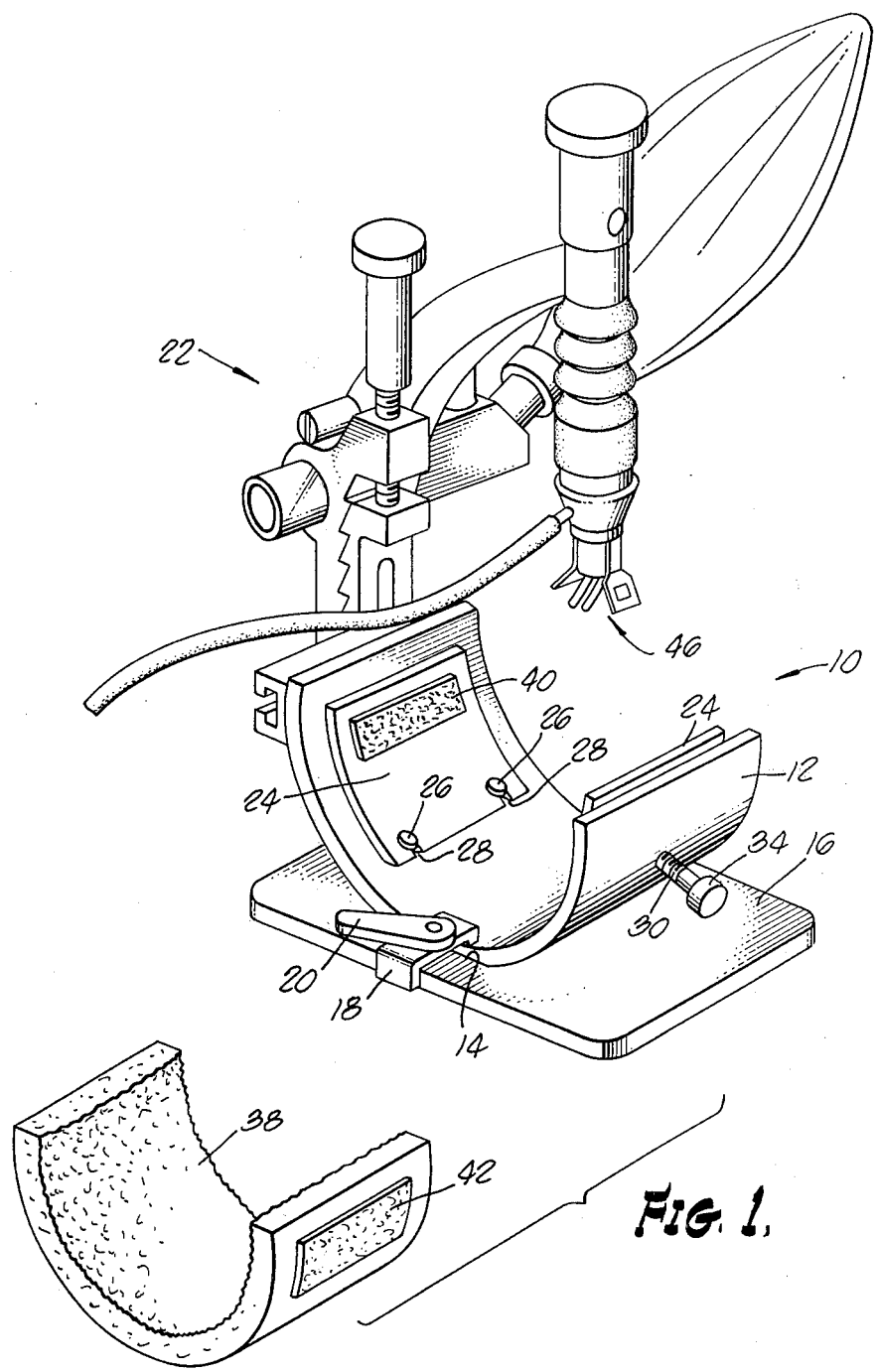
FIG. 1 is a perspective view of the head supporting and restraining apparatus of the present invention shown in conjunction wth a continuous positive airway delivery apparatus with which the head supporting and restraining apparatus of the present invention may be employed.
Figure 2:
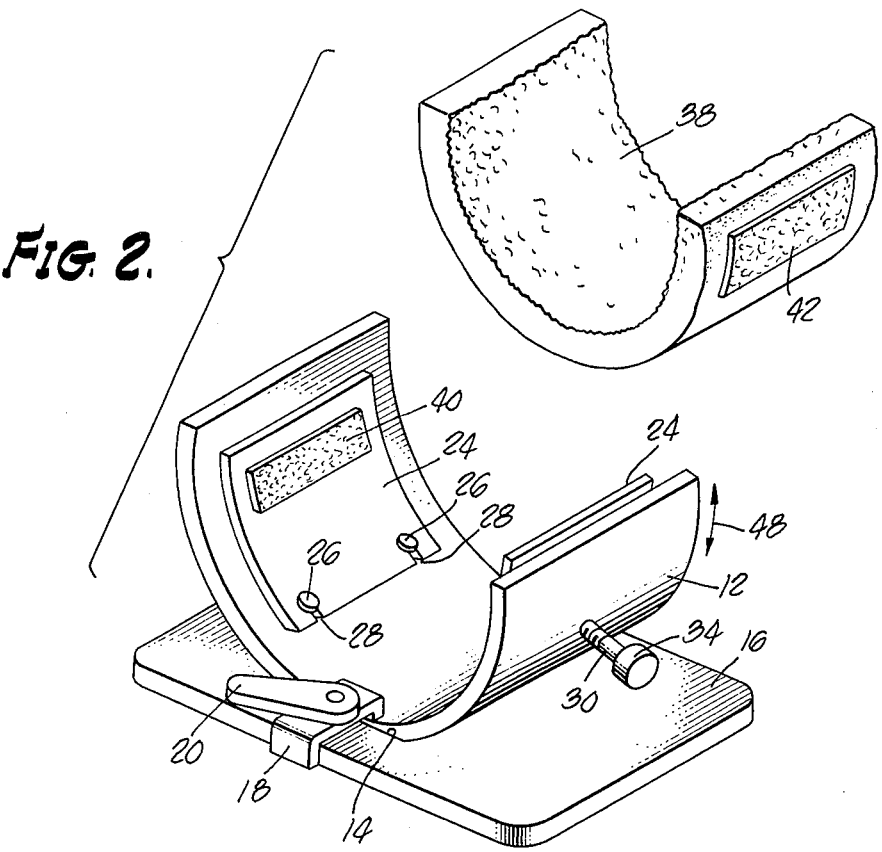
FIG. 2 is a perspective view of the head supporting and restraining apparatus of the present invention.

Referring now to the drawings, the head supporting and restraining apparatus 10 of the present invention is seen to comprise a generally arcuate or U-shaped cradle member 12 mounted in a generally arcuate groove 14 (FIG. 3) in a generally flat base member 16 by means of a suitable clamping device 18 (FIGS. 1 and 2). Clamping device 18 is secured to base member 16 by standard techinques, such as by a suitable adhesive, screws, etc. The cradle 12 may be rotated in the groove 14 to any one of a number of desired angular positions. A rotatable locking lever 20 forms part of the clamping device 18 and is provided so that the cradle 12 may be locked in any one of a number of desired angular positions rotation of locking lever 20 in the clockwise direction, for example, applying a clamping force to that portion of clamping device 18 which contacts cradle 12 whereby cradle 12 in turn is locked in a desired angular position, rotation of locking lever 20 in the counterclockwise direction removing the clamping force and allowing cradle 12 to be moved to a different angular position.

In FIG. 1, the head supporting and restraining apparatus 10 of the present invention is shown in conjunction with a continuous positive airway pressure delivery device 22 which is also mounted on the base member 16. However, it is contemplated that the head supporting and restraining apparatus 10 of the present invention may be used alone or with other types of medical devices.

A pair of generally arcuate head restraining plates 24, 24 are pivotably mounted to the interior surface of the cradle 12 by means of a pair of rivets 26, 26 which fit through slots 28, 28 in the lower edge of each of the restraining plates 24, 24.

In the preferred embodiment of the head supporting and restraining apparatus of the present invention the restraining plates 24, 24 are preferably constructed of a suitable flexible material, such as plastic, for example.

Figure 3:
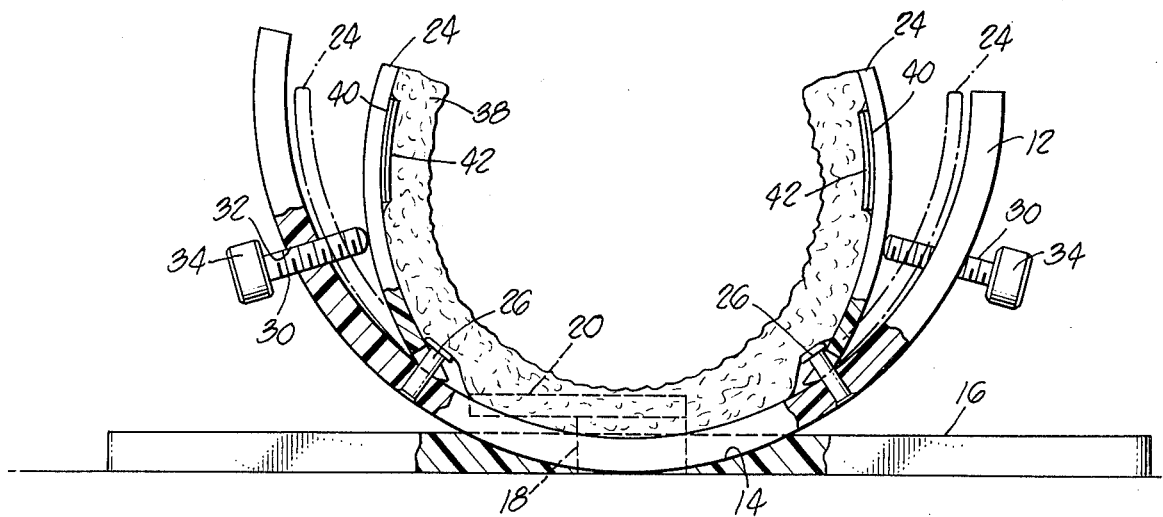
FIG. 3 is an end elevation view, partly in section, of the apparatus of the present invention with the head restraining plates shown in their inward position wherein they conform to and restrain a patient's head.

As best shown in FIG. 3, a screw member 30 extends through a threaded hole 32 on either side of the cradle member 12, Each screw 30 may be rotated, by means of a knob 34 on the end thereof, so as to move the generally flexible head restraining plates 24, 24 toward one another. Since the head restraining plates 24, 24 are constructed of a flexible material, such as plastic, the plates will return to their initial position (e.g., as shown in FIG. 2) lying against the interior surface of the cradle 12 (as shown in phantom lines in FIG. 3) when the screws 30, 30 are rotated so as to move radially outwardly of the cradle member 12.

A generally arcuate strip of a suitable padding material 38 lines the interior exposed surfaces of the restraining plates 24, 24 and the cradle 12 for cushioning the patient's head (not shown). One convenient way to removably secure the padding 38 in place is to provide mating velcro strips 40, 42 on the interior surface of each restraining plate 24 and the exterior surface of the padding 38, respectively.

In use, the head supporting and restraining apparatus 10 of the present invention is placed on a bed or table on which the patient whose head is to be supported and restrained will be laid. The patient is then laid on the bed with his head resting on the padding 38 which lines the interior, exposed surfaces of the restraining plates 24, 24 and the bottom exposed interior surface of the cradle 12. The screws 30, 30 are then turned in their respective internally threaded holes 32, 32 to move the padding-lined restraining plates 24, 24 toward one another, as best shown in FIG. 3, until the patient's head is gently, but firmly, supported and restrained.

Thereafter any suitable medical device (such as the nose cannula 46 of a continuous positive airway pressure delivery device 22, for example) may, if desired, be positioned and applied to the patient's head.

If and when it is desired to rotate the patient to any desired angular position, the locking lever 20 of the clamp 18 is loosened and the cradle 12 of the apparatus 10 may be rotated through an arcuate path (as shown by the arrows 48 in FIG. 2) to the angular position desired. The locking lever 20 may then be turned to firmly clamp the cradle 12 in that desired position.

While the head supporting and restraining apparatus of the present invention and has been shown in the drawings and described above with respect to one particular preferred embodiment thereof, it is to be understood that numerous variations, modifications and changes may be made to the preferred embodiment shown and described without departing from the spirit and scope of the present invention. Accordingly, it is intended that the scope of this patent be limited only by the scope of the appended claims.

We claim:
1. An apparatus for supporting and restraining the head of a patient during medical treament comprising:
   a base member,
   an outer support member mounted on said base member, said outer support member comprising a generally arcuate support member adapted to be moved in a generally arcuate path relative to said base member so as to position said arcuate support member in any one of a number of desired angular positions relative to said base member,
   means for holding said arcuate support member in a desired angular position,
   head restraint means mounted within said outer support member for restraining a patient's head, said restraint means including movable portions adapted to conform to and restrain a patient's head; and
   means for moving said movable portions of said head restraint means to positions wherein said restraint means will accommodate and restrain a patient's head.

2. An apparatus according to claim 1, wherein said means for holding said arcuate support member in a desired angular position comprises a clamp member operatively associated with said base member and said arcuate support member.

3. An apparatus according to claim 1, wherein said base member includes an upper surface having means defining an arcuate groove therein which receives a portion of said arcuate support member.

4. An apparatus according to claim 1, and further comprising padding means lining at least the portion of said head restraint means which are to contact a patient's head.

5. An apparatus according to claim 4, and further comprising detachable fastening means for removably attaching said padding to said restraint means.

6. An apparatus according to claim 5, wherein said detachable fastening means comprises complementary velcro strips secured to said padding and said restraint means, respectively.

7. An apparatus for supporting and restraining the head of a patient during medical treatment, comprising:
   a base member having a groove formed therein:
   a generally arcuate cradle member mounted on said base member within said groove for generally arcuate movement within said groove so as to be positioned in any one of a number of arcuate positions;
   means for locking said cradle member on said base member so that said cradle member is locked in a desired angular position within said groove relative to said base member;
   said cradle member being adapted to receive the head of a patient undergoing medical treatment, and
   restraint means operatively associated with said cradle member for restraining the movement of the head of a patient.

8. An apparatus for supporting and restraining the head of a patient during medical treatment, comprising:
   a base member;
   a generally arcuate cradle member mounted on said base member for generally arcuate movement so as to be positioned in any one of a number of angular positions;
   means for locking said cradle member on said base member so that said cradle member is locked in a desired angular position relative to said base member;
   restraining means mounted in and connected to said cradle member; said restraining means including spaced, relatively flexible portions movable toward one another so as to accommodate and restrain a patient's head; and
   means for moving said flexible poritons of said restraining means toward one another.

9. An apparatus for supporting and restraining the head of a patient during medical treatment, comprising:
   a generally flat base member having an upper surface; means defining a generally arcuate groove in said upper surface of said base member;
   a generally arcuate cradle member having a portion thereof resting in said generally arcuate groove in said upper surface of said base member; said cradle member including a generally arcuate bottom portion and a pair of generally arcuate, generally upstanding portions extending from said bottom portion; each of said generally upstanding portions having an upper end and a lower end; said upper ends of said generally upstanding portions defining an opening through which a patient's head may pass; said generally arcuate cradle member being movable, relative to said base member, on an arcuate path so that said opening of said cradle member may be disposed in any desired angular position;

a pair of generally arcuate, generally flexible restraining plates disposed within said cradle member; each of said restraining plates having its lower end pivotalby connected to said bottom portion of one of said generally upstanding portions of said cradle member; and a screw member extending through each of said upstanding portions of said cradle member; each said screw member having an inner end contacting one of said restraining plates; said screw member adapted to be screwed through their respective upstanding portions of said cradle member to move portions of said generally flexible restraining plates toward one another.

10. A device for supporting the head of a patient, comprising:

a base member having a groove formed therein;
a clamp member on said base member;
a generally U-shaped cradle member secured on said base member by said clamp member;
said clamp member being adjustable between an unlocked and locked position;
said clamp member, when in said unlocked position, permitting arcuate movement of said cradle member within said groove, whereby a head in said cradle may be rotated to a desired position by rotating said cradle member when said clamp member is in its said unlocked position.

11. An apparatus for supporiing and restraining the head of a patient during medical treatment comprising:

an outer support member having an interior, said support member comprising a generally arcuate member adapted to be moved through a generally arcuate path to position said support member in any one of a number of desired angular positions, a pair of restraining members mounted within the interior of said outer support member; and restraining members having portions thereof movable toward one another to firmly restrain movement of a patient's head inserted therebetween, and means for selectively moving said movable portions of said restraining members toward one another to positions wherein said restraining members may accomodate and restrain a patient's head.

12. Apparatus for supporting and restraining the head of a patient during medical treatment comprising:

an outer support member,
head restraint means mounted within said outer support member for restraining a patient's head, said restraining means comprising a pair of restraining members for receiving the head of a patient and having lower end portions pivotably connected to said outer support member, said restraining members being movable toward one another and comprising flexbile type material, and
means applied to said restraining members for moving said restraining members toward one another from an initial position wherein said restraining members accomodate and restrain a patient's head, said restraining members adapted to flex back towards said initial position when said moving means is not applied thereto.

* * * * *

UNITED STATES PATENT AND TRADEMARK OFFICE
CERTIFICATE OF CORRECTION

PATENT NO. : 4,019,727
DATED : April 26, 1977
INVENTOR(S) : William O. Martin and Harry Derda It is certified that error appears in the above-identified patent and that said Letters Patent are hereby corrected as shown below:

Col. 1, line 44: "adjustabe" should read "adjustable"
Col. 1, line 45: "and" should be deleted following the word "locking"
Col. 1, line 52: "mouted" should read "mounted"
Col. 2, line 32: "tions rotation" should read "tions, rotation"
Col. 3, line 33: "and" should be deleted following the word "invention"
Col. 3, line 44: "treament" should read "treatment"
Col. 4, line 51: "poritons" should read "portions"
Col. 5, line 2: "member, on" should read "member, in"
Col. 5, line 8: "pivotalby" should read "pivotably"
Col. 5, line 33: "supporiing" should read "supporting"
Col. 6, line 7: "and" should read "said"
Col. 6, line 15: "accomodate" should read "accommodate"
Col. 6, line 26: "flexbile" should read "a flexible"
Col. 6, line 30: "accomodate" should read "accommodate"

Signed and Sealed this nineteenth Day of July 1977

[SEAL]

Attest:

RUTH C. MASON
*Attesting Officer*

C. MARSHALL DANN
*Commissioner of Patents and Trademarks*